United States Patent
Wagner

(10) Patent No.: US 10,864,311 B2
(45) Date of Patent: Dec. 15, 2020

(54) DEVICE AND METHOD FOR EXTRACORPOREAL BLOOD TREATMENT

(71) Applicant: B. BRAUN AVITUM AG, Melsungen (DE)

(72) Inventor: André Wagner, Kassel (DE)

(73) Assignee: B. BRAUN AVITUM AG, Melsungen (DE)

( * ) Notice: Subject to any disclaimer, the term of this patent is extended or adjusted under 35 U.S.C. 154(b) by 465 days.

(21) Appl. No.: 15/906,447

(22) Filed: Feb. 27, 2018

(65) Prior Publication Data

US 2018/0250460 A1    Sep. 6, 2018

(30) Foreign Application Priority Data

Mar. 6, 2017  (DE) .......................... 10 2017 104 634

(51) Int. Cl.
| | |
|---|---|
| *A61M 1/16* | (2006.01) |
| *F04B 43/12* | (2006.01) |
| *F04B 53/20* | (2006.01) |

(52) U.S. Cl.
CPC ........ *A61M 1/1607* (2014.02); *A61M 1/1609* (2014.02); *A61M 1/1635* (2014.02);
(Continued)

(58) Field of Classification Search
CPC .............. A61M 1/1607; A61M 1/1609; A61M 1/1635; A61M 1/1639; A61M 2205/3331;
(Continued)

(56) References Cited

U.S. PATENT DOCUMENTS

| | | |
|---|---|---|
| 2005/0000868 A1 | 1/2005 | Weigel et al. |
| 2005/0131332 A1* | 6/2005 | Kelly ................. A61M 1/1633 604/4.01 |
| 2018/0043072 A1 | 2/2018 | Abel et al. |

FOREIGN PATENT DOCUMENTS

| | | |
|---|---|---|
| DE | 102015104431 A1 | 9/2016 |
| DE | 102015117396 A1 | 4/2017 |
| EP | 3156086 A1 | 4/2017 |

OTHER PUBLICATIONS

German Search Report for German Application No. 10 2017 104 634.8, with translation, dated Oct. 10, 2017—16 Pages.
(Continued)

*Primary Examiner* — Kai H Weng

(57) ABSTRACT

A device for extracorporeal blood treatment includes a balancing system and calculates an ultrafiltration volume $(UF_D)$ as a volume withdrawal on the basis of a pressure difference $(\Delta_P)$ and a temperature difference $(\Delta_T)$ at an inlet and an outlet of at least two balance chambers. To this end, pressure sensors are arranged directly behind an inlet and an outlet of the at least two balance chambers, respectively, and determine a fluid pressure at their respective position, and temperature sensors are arranged at inputs of the at least two balance chambers and determine a temperature in the inlet and the outlet of the balance chamber. The ultrafiltration volume $(UD_F)$ is calculated using the pressure difference $(\Delta_P)$ established on the basis of fluid pressure values determined by the pressure sensors, and the temperature difference $(\Delta_T)$ established on the basis of temperature values determined by the temperature sensors.

7 Claims, 2 Drawing Sheets

(52) U.S. Cl.
CPC ........... *A61M 1/1639* (2014.02); *F04B 43/12* (2013.01); *F04B 53/20* (2013.01); *A61M 2205/3331* (2013.01); *A61M 2205/3337* (2013.01); *A61M 2205/3351* (2013.01); *A61M 2205/3355* (2013.01); *A61M 2205/3368* (2013.01); *A61M 2205/3372* (2013.01); *A61M 2205/3386* (2013.01); *A61M 2205/3606* (2013.01)

(58) Field of Classification Search
CPC .. A61M 2205/3337; A61M 2205/3351; A61M 2205/3355; A61M 2205/3368; A61M 2205/3372; A61M 2205/3386; A61M 2205/3606; F04B 43/12; F04B 53/20
See application file for complete search history.

(56) References Cited

OTHER PUBLICATIONS

Extended European Search Report for European Application No. 18 158 427.7, dated Jul. 9, 2018, with English translation, 17 pages.

\* cited by examiner

DEVICE AND METHOD FOR EXTRACORPOREAL BLOOD TREATMENT

CROSS REFERENCE TO RELATED APPLICATIONS

This application claims priority to German application DE 10 2017 104 634.8 filed Mar. 6, 2017, the contents of such application being incorporated by reference herein.

FIELD OF THE INVENTION

The invention relates to a device and a method for the extracorporeal blood treatment and refers in particular to a device and a method for or with extracorporeal blood treatment for obtaining a volume withdrawal using a balance chamber circuit.

In the extracorporeal blood treatment and in particular in dialysis, a balancing means or balancing system has the task to transport the prepared dialysis liquid continuously to a dialyzer and through the dialyzer to an outflow. The balancing means has to ensure here that the fluid volume supplied to the dialyzer is equal to the fluid volume withdrawn from the dialyzer. In addition, a metering pump or ultrafiltration pump is arranged to withdraw a defined ultrafiltration volume from a patient for the duration of a therapy (volume withdrawal). This ultrafiltration volume is not detected by the balancing means, so that the withdrawn fluid volume depends exclusively on the ultrafiltration pump.

In the field of the extracorporeal blood treatment, for instance, membrane-less balancing methods as well as balancing methods involving high-precision mutual/reciprocal/alternating pumps are known.

By way of example, a known membrane-less assembly or a method using such assembly which are based on a Coriolis measuring cell, utilizes the Coriolis effect with electromagnetic flow meters or mass flow meters on the basis of the inertia force of fluids in oscillating pipelines. Such assemblies may indeed be precise, but are commonly prone to failure and are not sufficiently stable for being used in dialysis apparatus in every case.

Another exemplarily known assembly concerning mutual pumps or a corresponding method is based on the duplex pump technology in which a balancing system comprises a doubly provided piston stroke pump. While one of the two piston stroke pumps delivers a predefined measured amount of dialysis liquid to the dialyzer into a closed system, the second piston stroke pump withdraws from the closed system exactly the same amount of used dialysis liquid. The disadvantage consists here in the need of maintenance on a regular basis.

A known balancing system or balance chamber system or balancing chamber system comprises two balance chambers which alternately feed and discharge the dialysis liquid to and from the dialyzer.

In the known system, a first balance chamber and a second balance chamber are substantially provided, each of which being subdivided in two chambers with an elastic membrane and comprising two inlets and two outlets which each can be opened or closed by a magnet valve. The membranes of the balance chambers always expand in opposite directions. A first flow pump transports used dialysis liquid toward the first balance chamber and at the same time pushes fresh dialysis liquid to a dialyzer, and a second flow pump transports fresh dialysis liquid coming from a dialysis liquid treatment unit of the apparatus toward the second balance chamber and at the same time pushes used dialysis liquid into the outlet. A dialysate pressure sensor is arranged to measure the pressure in the effluent dialysis liquid behind the dialyzer. Further arranged is an air separator for separating air from the dialysis liquid.

In a closed liquid circuit (closed system) for dialysis liquid, the inflowing amount of liquid exactly corresponds to the outflowing amount of liquid. It is only the ultrafiltration pump (UF pump) which is able to withdraw liquid from this circuit. In other words, the actual ultrafiltration volume is bypassed around the balance chamber with a (volumetric) ultrafiltration pump (for instance a rotary slide piston pump) which takes liquid from the closed circuit and hence controls the ultrafiltration, in this way providing for the actual withdrawal of liquid from the patient via the semipermeable membrane of the dialyzer.

As balance chamber systems as well as ultrafiltration pumps show certain tolerances, it is disadvantageous here that there are deviations from the set ultrafiltration amount.

SUMMARY OF THE INVENTION

The invention is thus based on the object to provide an alternative to the known system of withdrawing the volume with an ultrafiltration pump.

According to aspects of the invention, this object is achieved by a device and by a method for extracorporeal blood treatment comprising the features of the independent claims. Advantageous further developments of the invention are subject-matter of the independent claims.

According to one underlying inventive idea, the arranging of two proportional pressure valves in the inlet and outlet of the balance chambers allows a volume withdrawal from the patient or a volume supply to the patient by a specifically adjustable or adjusted pressure difference between the two balance chambers by the expansion of the materials of the balance chambers.

Moreover, using a heating element or a cooling element, for instance with a heat exchanger in the outlet of the balance chambers, allows to deliberately generate a temperature difference between balance chamber inlet and balance chamber outlet, which in turn results in a volume withdrawal from or a volume supply to the patient due to the difference in density of liquids having differing temperatures.

The previously described way allows according to aspects of the invention to save the ultrafiltration pump in the balance chamber circuit or at least bypass it, and at least the withdrawal of liquid can be achieved while omitting the ultrafiltration pump or at least bypassing it. The invention thus offers an alternative to a volume withdrawal on the basis of the operation of an ultrafiltration pump, with the option that the ultrafiltration pump is still provided such that it may be bypassed, for instance, or is omitted.

According to aspects of the invention, there is the advantage that the assembly may do without the ultrafiltration pump, faulty ultrafiltration due to differences in density and pressure are prevented, the assembly does not need further constant pressure valves, the volume withdrawal is possible through a cooling with a heat exchanger in return for intake of water, and that there is applicability both for hemodialysis, hemodiafiltration as well as hemofiltration.

Specifically, the object is achieved by a device for extracorporeal blood treatment including a balancing system, the device being arranged to calculate an ultrafiltration volume as a volume withdrawal on the basis of a pressure difference and a temperature difference at an inlet and an outlet of at least two balance chambers of the balancing system.

Preferably, the device for extracorporeal blood treatment further comprises a first pressure sensor and a second pressure sensor which are each arranged directly behind the inlet and outlet of the at least two balance chambers, respectively, the first pressure sensor and the second pressure sensor being arranged to determine a fluid pressure at their position; a first temperature sensor and a second temperature sensor at inputs of the at least two balance chambers, the first temperature sensor and the second temperature sensor being arranged to determine a temperature in the inlet and the outlet of the balance chamber; and a calculation device for calculating an ultrafiltration volume using the pressure difference which can be established on the basis of fluid pressure values determined by the first pressure sensor and the second pressure sensor, and the temperature difference which can be established on the basis of temperature values determined by the first temperature sensor and the second temperature sensor.

Preferably, the ultrafiltration pump is omitted or at least arranged such that it can be bypassed.

Preferably, a first proportional valve and a second proportional valve are arranged to control a pressure difference required for reaching a volume withdrawal by continuously adjusting a pressure at the positions of the first pressure sensor and the second pressure sensor respectively.

Preferably, the first proportional valve and the second proportional valve can be dynamically controlled.

Preferably, a heating element and/or cooling element is/are arranged for creating and/or controlling a targeted temperature difference between the balance chamber inlet and balance chamber outlet in the outlet of the balance chambers, the heating element and/or cooling element preferably being a heat exchanger.

The calculation of the volume withdrawal is carried out on the basis of the following formula:

$$UF_D = a * \Delta_P * DF_F + b * \Delta_T * DF_F$$

wherein $UF_D$ is the ultrafiltration volume, $\Delta_P$ is the pressure difference, $\Delta_T$ is the temperature difference, a and b are coefficients, and $DF_F$ is a dialysis liquid volume.

The pressure difference and the temperature difference preferably are proportional to the ultrafiltration volume.

According to aspects of the invention, an object is achieved by a method for calculating an ultrafiltration volume as a volume withdrawal in a device for extracorporeal blood treatment comprising a balancing system, including the step of calculating the ultrafiltration volume on the basis of a pressure difference and a temperature difference at an inlet and an outlet of at least two balance chambers of the balancing system.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
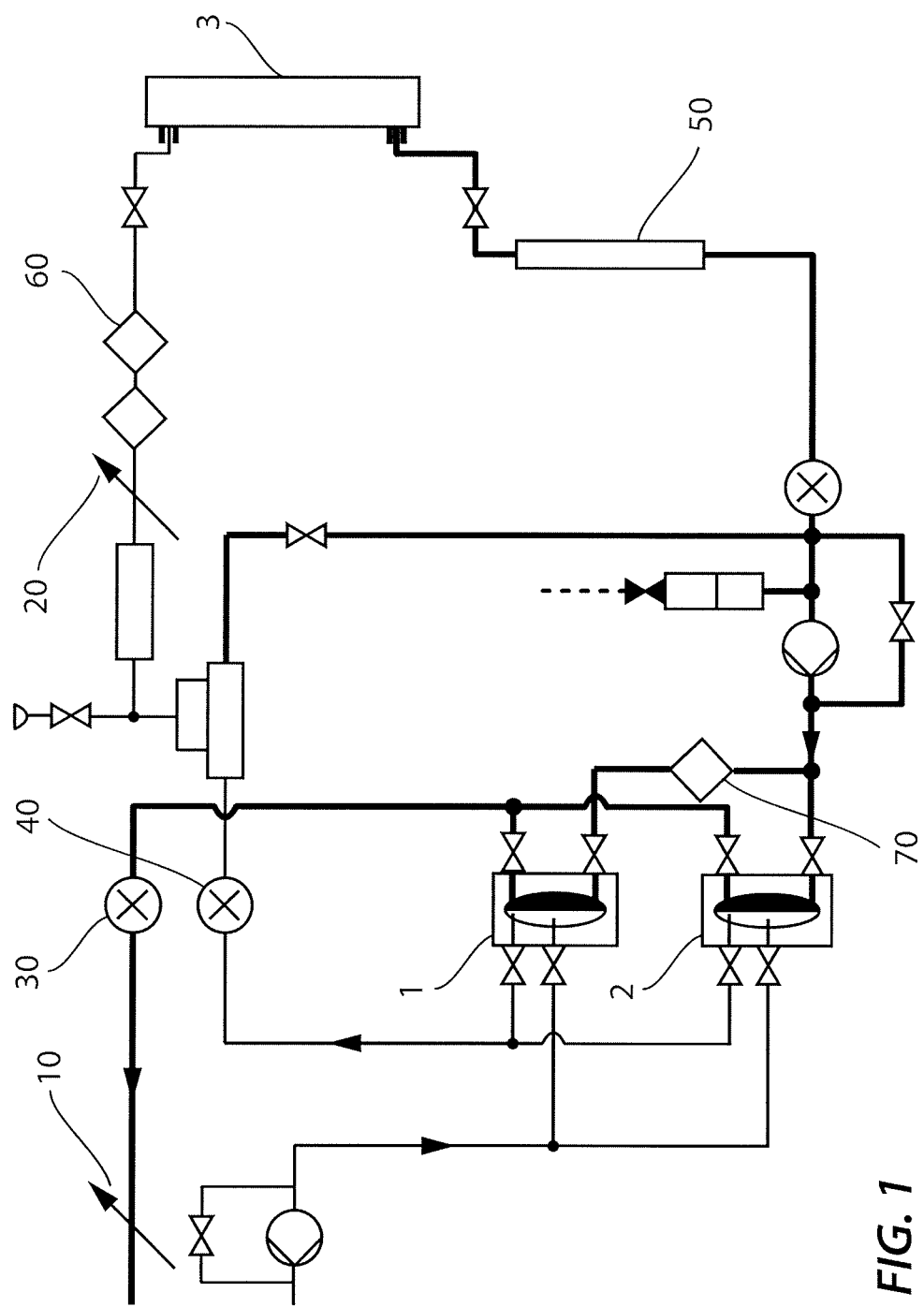
FIG. 1 shows a schematic and partial hydraulic chart of a balancing system according to one embodiment, which may be provided in a device for extracorporeal blood treatment.

In accordance with FIG. 1, a balancing system or balance chamber system or balancing chamber system for extracorporeal or with an extracorporeal blood treatment according to an exemplary embodiment, which may form part of a device for extracorporeal blood treatment such as a dialysis machine, for instance, comprises a first balance chamber 1 and a second balance chamber 2. A dialyzer is designated with the reference symbol 3. Components of the system shown in FIG. 1 which are known per se and do not have any substantial effect in the context of the invention are not denoted with reference symbols and expediently not described in further detail.

A first pressure sensor 30 (PDA2) and a second pressure sensor 40 (PDE) are arranged directly behind the inlet and outlet of the balance chamber 1, 2 for continuously determining the pressure at their arrangement position or at this respective place.

Further, a first proportional valve 10 (Prop1) and a second proportional valve 20 (Prop2) are arranged to continuously adjust the pressure to therapy requirements (required pressure difference for reaching a volume withdrawal).

The first and the second proportional valve 10, 20 replace known constant pressure valves and can be controlled in a dynamic manner.

The fluid pressure directly depends on a preset flow rate, on the one hand, and on aging conditions of components such as dialysis liquid filters, on the other hand. In addition, specific pressure alterations on the blood side due to the venous backflow pressure (PV) or the arterial inflow pressure (PBE, pressure at blood entrance) also have a direct effect on the pressure of the dialysis liquid when entering (PDE).

A temperature difference at the two inputs of the balance chamber(s) 1, 2 is determined as well. The temperature difference is established on the basis of a temperature detection with a first temperature sensor 70 (TSDA) and a second temperature sensor 60 (TSD-S).

As illustrated in FIG. 1, the first pressure sensor 30 and the first proportional valve 10 are arranged in a common outlet branch downstream of the balance chambers 1, 2 (greater line thickness), and the second pressure sensor 40 and the second proportional valve 20 are arranged in a common inlet branch (for the inlet of fresh dialysis liquid to the dialyzer 3, equivalent to the outlet branch leading away from the balance chambers 1, 2 and the inlet branch for the fresh dialysis liquid to the dialyzer 3 downstream of the balance chambers 1, 2, finer line thickness). Furthermore, the second temperature sensor 70 is arranged in a common inlet branch upstream of the balance chambers 1, 2 (greater line thickness), and the first temperature sensor 60 is arranged in the same fluid path as the second pressure sensor 40 and the second proportional valve 20 (finer line thickness).

The arrangement of the afore-mentioned components in each of the common branches for both balance chambers 1, 2 results for instance from the fact that the individual balance chambers work cyclically and complementarily with respect to each other (respectively one of the balance chambers receives fresh dialysis liquid and pushes the used dialysis liquid into the outlet with the membrane displacement, and the respectively other balance chamber receives used dialysis liquid and pushes fresh dialysis liquid toward the dialyzer 3 via the membrane displacement) in order to ensure a continuous flow into the dialyzer 3. This is why the pressure sensors 30, 40, the proportional valves 10, 20 and the temperature sensors 60, 70 are arranged in branch sections through which fluid flows from or to both balance chambers 1, 2.

In the outflow of (/to) the balance chamber 1, 2, i.e. downstream of the dialyzer 3, a heating element or a cooling element 50 is further arranged, with which a particular temperature difference required for achieving a certain volume withdrawal can be controlled or adjusted.

A calculation of the volume withdrawal due to the pressure difference and temperature difference is carried out on the basis of the following formula (1):

$$UF_D = a * \Delta_P * DF_F + b * \Delta_T * DF_F \quad (1),$$

wherein $UF_D$ is the ultrafiltration volume, $\Delta_P$ is the pressure difference, $\Delta_T$ is the temperature difference, a and b are coefficients, and $DF_F$ is a dialysis liquid volume.

Figure 2:
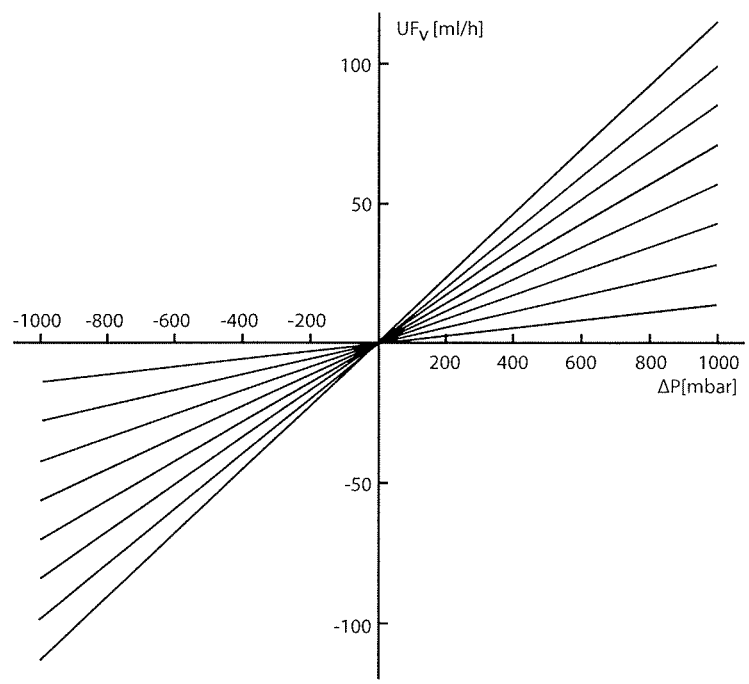
FIG. 2 schematically shows a characteristic curves diagram of a pressure dependence of an ultrafiltration volume according to the exemplary embodiment.
Figure 3:
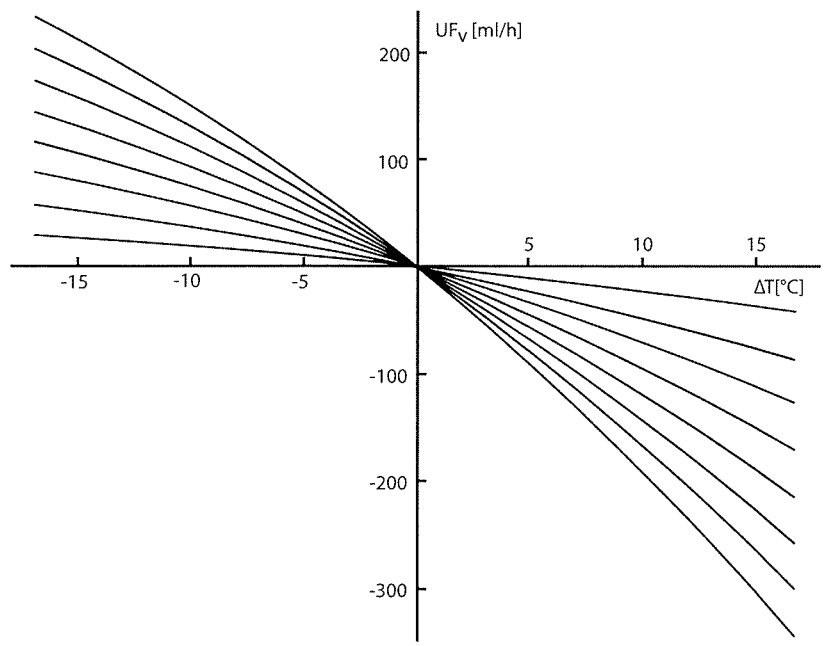
FIG. 3 schematically shows a characteristic curves diagram of a temperature dependence of an ultrafiltration volume according to the exemplary embodiment.

The pressure difference $\Delta_P$ and the temperature difference $\Delta_T$ are proportional to the ultrafiltration volume $UF_D$, such as schematically illustrated in FIGS. 2 and 3, for example.

A calculation device for carrying out the aforementioned calculation is integrated or realized in hardware and/or software form in processing components of the device, for instance a controlling device, a processor device and the like, and as such not further illustrated.

In other words, required temperature and pressure differences are each adjusted according to the exemplary embodiment via the proportional valves 10, 20 respectively and the heating element and/or cooling element 50 in the outflow with a predetermined control process, and an arising volume withdrawal for the resulting temperature and pressure differences is calculated.

As described above, the control of the pressure-dependent and temperature-dependent volume withdrawal is performed on the basis of a determination of the pressure conditions in front of and behind the balance chamber 1, 2 with a pressure sensor for the pressure of the dialysis liquid when entering (PDE) and a second pressure sensor for the pressure of the dialysis liquid when exiting (PDA2), and on the basis of a determination of the temperature conditions with a configured temperature sensor unit which consists of a temperature sensor (TSD-S) and a further temperature sensor (TSDA) and is installed in the apparatus for extracorporeal blood treatment, such as a dialysis machine, for instance. The above-mentioned pressure sensors 30, 40 allow the determination of the pressure difference in front of and behind the balance chamber.

Further, a proportional valve 10, 20 for pressure control is arranged both in the inflow and the outflow of the balancing chamber, and a heating element or cooling element 50 such as a heat exchanger is provided for controlling the temperature difference in the outflow.

Thus, the previously described balancing system or balance chamber system for extracorporeal blood treatment may do without an ultrafiltration pump, or the latter may be installed and configured such that it can be bypassed at least.

It should be understood that the invention is not limited to the exemplary embodiment described above, but alterations and modifications may be apparent for the person skilled in the art without departing from the outlined scope of the invention.

It is conceivable, for instance, to design the previously described alternative for the determination of the volume withdrawal for existing devices in such a manner that it can be retrofitted with only one ultrafiltration pump and, if need be, with parts of the required sensor and control systems. In this case, it may be sufficient to subsequently install parts of the required sensor and control systems which are not present yet, and to provide a switchable bypass on the ultrafiltration pump.

As described above, a device for extracorporeal blood treatment comprises a balancing system and calculates an ultrafiltration volume ($UF_D$) as a volume withdrawal on the basis of a pressure difference ($\Delta_P$) and a temperature difference ($\Delta_T$) at an inlet and an outlet of at least two balance chambers (1, 2). To this end, a first pressure sensor (30) and a second pressure sensor (40) are each arranged directly behind an inlet and an outlet of at least two balance chambers (1, 2), respectively, and determine a fluid pressure at their respective position, and a first temperature sensor (60) and a second temperature sensor (70) are arranged at inputs of the at least two balance chambers (1, 2) and determine a temperature in the inlet and the outlet of the balance chamber. The ultrafiltration volume ($UD_F$) is calculated using the pressure difference ($\Delta_P$) which can be established on the basis of fluid pressure values determined by the first pressure sensor (30) and the second pressure sensor (40), and the temperature difference ($\Delta_T$) which can be established on the basis of temperature values determined by the first temperature sensor (60) and the second temperature sensor (70).

The invention claimed is:

1. A device for extracorporeal blood treatment, the device comprising:
   a balancing system including at least two balancing chambers;
   a first pressure sensor arranged at an inlet of each of the at least two balance chambers and a second pressure sensor arranged at an outlet of each of the at least two balance chambers, the first pressure sensor and the second pressure sensor configured to determine a fluid pressure at their position;
   a first temperature sensor and a second temperature sensor at inputs of the at least two balance chambers, the first temperature sensor and the second temperature sensor being arranged to determine a temperature in the inlet and the outlet of each of the at least two balance chambers; and
   a calculation device for calculating an ultrafiltration volume using a pressure difference established based on fluid pressure values determined by the first pressure sensor and the second pressure sensor, and a temperature difference based on temperature values determined by the first temperature sensor and the second temperature sensor,
   the calculation device arranged to calculate the ultrafiltration volume as a volume withdrawal based on the pressure difference and the temperature difference at the inlet and the outlet of each of the at least two balance chambers of the balancing system,
   wherein the calculation of the volume withdrawal is carried out based on the following formula:

$$UF_D = a * \Delta_P * DF_F + b * \Delta_T * DF_F,$$

wherein $UF_D$ is the ultrafiltration volume, $\Delta_P$ is the pressure difference, $\Delta_T$ is the temperature difference, a and b are coefficients, and $DF_F$ is a dialysis liquid volume.

2. The device for extracorporeal blood treatment according to claim 1, in which an ultrafiltration pump is omitted or arranged such that said ultrafiltration pump is bypassed.

3. The device for extracorporeal blood treatment according to claim 1, further comprising:
   a first proportional valve and a second proportional valve arranged to control a pressure difference required for reaching a volume withdrawal by continuously adjusting a pressure at each of the positions of the first pressure sensor and the second pressure sensor.

4. The device for extracorporeal blood treatment according to claim 3, wherein the first proportional valve and the second proportional valve are dynamically controllable.

5. The device for extracorporeal blood treatment according to claim 1, further comprising:

at least one of a heating element or a cooling element arranged in the outlet of the balance chambers for at least one of creating or controlling a targeted temperature difference between the balance chamber inlet and balance chamber outlet.

6. The device for extracorporeal blood treatment according to claim 1, wherein the pressure difference and the temperature difference are proportional to the ultrafiltration volume.

7. A method for calculating an ultrafiltration volume as a volume withdrawal in a device for extracorporeal blood treatment including a balancing system comprising at least two balancing chambers, the method comprising the steps of:

measuring a first pressure at an inlet of each of the at least two balance chambers using a first pressure sensor arranged at the inlet;

measuring a second pressure at an outlet of each of the at least two balance chambers using a second pressure sensor arranged at the outlet;

measuring a first temperature at the inlet of each of the at least two balance chambers using a first temperature sensor arranged at the inlet;

measuring a second temperature at the outlet of each of the at least two balance chambers using a second temperature sensor arranged at the outlet; and calculating the ultrafiltration volume based on a pressure difference and a temperature difference at the inlet and the outlet of the at least two balance chambers of the balancing system, wherein the calculation of the volume withdrawal is carried out based on the following formula:

$$UF_D = a * \Delta_P * DF_F + b * \Delta_T * DF_F,$$

wherein $UF_D$ is the ultrafiltration volume, $\Delta_P$ is the pressure difference, $\Delta_T$ is the temperature difference, a and b are coefficients, and $DF_F$ is a dialysis liquid volume.

* * * * *